United States Patent [19]

Drake

[11] Patent Number: 4,480,141
[45] Date of Patent: Oct. 30, 1984

[54] CLEAVAGE OF HYDROPEROXIDES

[75] Inventor: Charles A. Drake, Bartlesville, Okla.

[73] Assignee: Phillips Petroleum Company, Bartlesville, Okla.

[21] Appl. No.: 507,398

[22] Filed: Jun. 24, 1983

[51] Int. Cl.$^3$ ............................................. C07C 37/08
[52] U.S. Cl. ..................................... 568/798; 568/385
[58] Field of Search ................ 568/741, 768, 798, 385

[56] References Cited

U.S. PATENT DOCUMENTS

| | | | |
|---|---|---|---|
| 2,628,983 | 2/1953 | Aller et al. | 568/798 |
| 2,628,984 | 2/1953 | Aller et al. | 568/798 |
| 2,683,751 | 7/1954 | Filar | 568/798 |
| 2,748,172 | 5/1956 | Rodgers | 568/798 |
| 2,951,870 | 9/1960 | Cooke | 568/798 |
| 3,497,561 | 2/1970 | Gelbein | 568/798 |
| 3,959,381 | 5/1976 | Arkell et al. | 568/798 |
| 4,209,465 | 6/1980 | Austin et al. | 568/798 |

Primary Examiner—Werren B. Lone

[57] ABSTRACT

Secondary alkyl-substituted hydroperoxides are cleaved to phenols and ketones by contacting the secondary alkyl-substituted benzene hydroperoxide with boron phosphate, at a temperature of from about 20°–200° C.

9 Claims, No Drawings

CLEAVAGE OF HYDROPEROXIDES

This invention relates to the cleavage of hydroperoxides.

The use of aqueous acid catalyst systems such as $H_2SO_4$ and water for the cleavage of hydroperoxides to phenols and ketones is well known in the art. While such a catalyst system is operable for its intended use, it is not without disadvantages.

An aqueous acid catalyst system tends to make product separation (i.e. phenols and ketones) difficult because a neutralization step is frequently required. Furthermore, the use of aqueous acid systems sometimes results in the formation of azeotropes such that the products cannot be separated by either simple or fractional distillation. Therefore, a catalyst system which gives good yields and selectivities to phenols and ketones from the cleavage of hydroperoxides but avoids the problems mentioned above is highly desirable.

It is therefore an object of this invention to provide an improved process for the cleavage of hydroperoxides to phenols and ketones.

Other aspects, objects, and advantages of the present invention are apparent from the specification and claims.

In accordance with the present invention, I have discovered that secondary-alkyl substituted benzene hydroperoxides are effectively cleaved by contacting the hydroperoxide with boron phosphate.

By utilizing a boron phosphate catalyst, relatively short reaction times, moderate reaction temperatures, and easy product separation are accomplished.

The secondary alkyl substituted benzene hydroperoxides contemplated for use in the present invention are represented by the general formulae:

$$\text{(I)} \quad \text{R'}_2\text{C(OOH)}-\text{C}_6\text{H}_{5-n}(\text{R})_n \qquad \text{or} \qquad \text{(II)}$$

wherein R is a $C_1$-$C_{20}$ alkyl, cycloalkyl, or alkaryl radical, R' is independently a $C_1$ to $C_{10}$ alkyl, aryl, or alkaryl radical, R'' is independently H or a $C_1$ to $C_{10}$ alkyl, aryl, or alkaryl radical, n is an integer from 0–5, and x is an integer from 2 to 11. Exemplary compounds falling under formulae (I) or (II) suitable for use in the present invention include cyclohexylbenzene hydroperoxide, cumene hydroperoxide, sec-butylbenzene hydroperoxide, sec-pentylbenzene hydroperoxide, and sec-hexylbenzene hydroperoxide with cyclohexylbenzene hydroperoxide being preferred.

Boron phosphate is commercially available, for example, from Alfa Products, Thiokol/Ventron Division, Danvers, Mass.

Preferably, the contacting is carried out in the presence of an aromatic hydrocarbon or ketone solvent.

Aromatics contemplated for use in the present invention are represented by the following general formula:

$$\text{(III)} \quad C_6H_{6-m}(R''')_m$$

wherein R''' is a $C_1$ to $C_8$ hydrocarbyl radical and m is a whole number from 0–6. Examples of such aromatics include benzene, toluene, m-xylene, p-xylene, and isopropyl benzene and mixtures thereof.

Ketones useful in the present invention contain from 3 to 10 carbon atoms. Examples include acetone, methyl ethyl ketone, methyl isobutyl ketone and mixtures thereof.

In the present invention the compounds of formulae (I) or (II) are cleaved to phenols and ketones. For example, cyclohexylbenzene hydroperoxide is cleaved to phenol and cyclohexanone.

The process of the present invention is carried out by contacting the secondary-alkyl substituted benzene hydroperoxide with the boron phosphate at a temperature in the broad range of from about 20°–200° C., with 60–100° C. preferred.

Typically about 0.1–10 weight percent, preferably 1–3 weight percent of the boron phosphate is employed based upon the weight of the secondary-alkyl substituted benzene hydroperoxide to be decomposed.

The cleavage process can be carried out either batchwise or continuously, using a fixed catalyst bed, stirred batch reactor, a fluidized catalyst chamber, or any other suitable contacting techniques.

Generally, the reaction time will be from about 5 minutes to 5 hours, preferably from about 30 to 120 minutes.

Generally, the liquid hourly space velocity, LHSV, will be from about 0.1–10 with about 0.2–4 preferred.

While the pressure at which the process of the present invention is carried out is not though to be critical, it is broadly from about sub-atmospheric to 1000 psig with about atmospheric to 50 psig preferred to ensure maximum product formation.

The reaction products may be isolated by conventional procedures such as distillation and extraction. The residual products, can, if desired, be purified by conventional procedures such as column chromatography or fractional recrystallization.

The following examples illustrate the present invention.

EXAMPLE I

Preparation of Cyclohexylbenzene hydroperoxide

The cyclohexylbenzene hydroperoxide (CHBHP) feed employed in the following cleavage reaction was pooled from numerous laboratory investigations on the oxidation of cyclohexylbenzene (CHB), such as the following exemplary preparations. The pooled feed had a CHBHP concentration of 8.7 wt % in unreacted cyclohexylbenzene.

(A) Atmospheric oxidation of CHB:

A 300 mL 3-neck round bottom flask equipped with a dispersion tube and a magnetic stirrer was charged with 199 g of CHB and 1 g of cumene hydroperoxide. The flask was heated to 130° C. and $O_2$ introduced via the dispersion tube at about 0.8 standard cubic feet per hour (SCFH). Reaction was carried out for four hours at 130° C. and atmospheric pressure, then reactor contents sampled and analyzed by gas liquid chromatography (GLC) using an internal standard. Typical CHB conversions of about 28% with selectivity to CHBHP of about 70% were obtained.

(b) CHB oxidation under pressure:

A 300 mL stainless steel Autoclave Engineers Magnedrive stirred tank reactor was charged with 49 g of cyclohexylbenzene and 1 g of cumene hydroperoxide. The reactor was then sealed, pressurized with $O_2$ to about 180 psig, and heated to about 120° C. for four hours. Typical CHB conversions of about 17% with selectivity to CHBHP of about 74% were obtained.

This example describes the typical preparations of the cyclohexylbenzene hydroperoxide employed in the following cleavage runs.

EXAMPLE II

Catalyst Preparation

The catalyst employed for cleavage of cyclohexylbenzene hydroperoxide were prepared as follows.

Catalyst A was prepared by wetting 9 g of finely powdered Filtrol 24 acidic clay (marketed by Filtrol Corporation) with 1 g of $H_3PO_4BF_3$ complex in an inert ($N_2$) atmosphere.

Catalyst B boron phosphate was employed as received from Alfa Products, Thiokol/Ventron Division, Danvers, Massachusetts (cat. #14103).

EXAMPLE III

General Reaction Procedure

All cyclohexylbenzene hydroperoxide cleavage reactions were carried out in a 100 mL round bottom flask equipped with a magnetic stir bar. Generally, about 14 g of crude oxidation product (see Example I), 0.4 of internal standard (n-pentylbenzene), 0.1–3.0 g of catalyst and about 10 ml of solvent were charged to the vessel. The reactor contents were stirred at room temperature up to about 70° C. for 30 minutes to about 2 hours, then sampled for analysis by gas liquid chromatography (glc). The product yields are corrected for the fact that only 90% of the hydroperoxide in the CHBHP feed is the correct hydroperoxide, i.e.

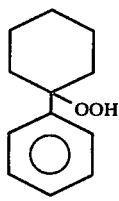

Other isomeric hydroperoxides are incapable of cleavage to give the desired ultimate products, phenol and cyclohexanone.

EXAMPLE IV

CHBHP Cleavage

Several cleavage reactions were carried out employing the catalysts described in Example II according to the general procedure set forth in Example III. Amount of catalyst used, solvents employed, reaction time and temperature as well as product analyses are summarized in the Table.

TABLE

| Run | Catalyst, g | CHBHP Chgd, g | Solvent, mL | Reaction Temp °C. | Time min | Yield % Phenol | Cyclohexanone |
|---|---|---|---|---|---|---|---|
| 1* | $BF_3.H_3PO_4$, 0.05 | 14.3 | Acetone, 10 | 25 | 60 | 41 | 41 |
|  |  |  |  |  | 120 | 57 | 59 |
| 2 | A, 3.0 | 14.5 | Acetone, 10 | 25 | 60 | 73 | 76 |
|  |  |  |  |  | 120 | 87 | 86 |
| 3 | B, 0.5 | 14.2 | Acetone, 10 | 25 | 60 | 27 | 26 |
|  |  |  |  |  | 120 | 28 | 27 |
| 4 | B, 0.5 | 14.2 | Acetone, 10 | 60 | 60 | 79 | 83 |
|  |  |  |  |  | 120 | 88 | 94 |
|  |  |  |  |  | 180 | 93 | 99 |
| 5 | B, 0.2 | 14.2 | MEK**, 10 | 70 | 60 | 86 | 83 |
|  |  |  |  |  | 120 | 99 | 97 |

*Unsupported $BF_3.H_3PO_4$ complex used as cleavage catalyst
**methyl ethyl ketone The results of these experiments demonstrate that boron phosphate in an active and selective catalyst for the cleavage of cyclohexylbenzene hydroperoxide to give phenol and cyclohexanone, especially at reaction temperatures above about 60° C. (see Runs 4 and 5).

Reasonable variations and modifications are possible from the foregoing disclosure without departing from the spirit and scope of the present invention.

I claim:

1. A process for the formation Ketone and phenols by the cleavage of a secondary alkyl substituted benzene hydroperoxide of the formulae:

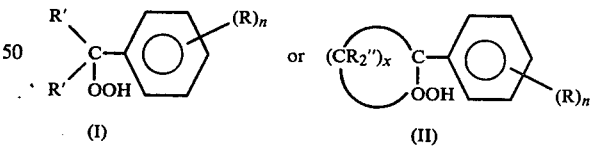

wherein R is a $C_1$–$C_{20}$ alkyl, cycloalkyl, or alkaryl radical, R' is independently a $C_1$ to $C_{10}$ alkyl, aryl, or alkaryl radical, R" is independently H or a $C_1$ to $C_{10}$ alkyl, aryl, or alkaryl radical, n is an integer from 0–5, and x is an integer from 2 to 11, which comprises contacting said secondary-alkyl substituted benzene hydroperoxide with about 0.1–10 weight percent boron phosphate, based on the weight of said secondary-alkyl substituted benzene hydroperoxide, at a temperature of from about 20°–200° C.

2. A process according to claim 1 carried out in the presence of at least one solvent selected from the group consisting of:

(a) an aromatic hydrocarbon of the formula

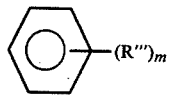

wherein R''' is a $C_1$ to $C_8$ hydrocarbyl radical and m is a whole number from 0-6; and (b) a $C_3$ to $C_{10}$ ketone.

3. A process according to claim 1 wherein said secondary-alkyl substituted benzene hydroperoxide is cyclohexylbenzene hydroperoxide.

4. A process according to claim 1 wherein said solvent is acetone.

5. A process according to claim 1 wherein said solvent is a methylethyl ketone.

6. A process according to claim 1 wherein said temperature is from about 60° C. to about 100°C.

7. A process according to claim 1 wherein said boron phosphate is employed in an amount of from about 1 to 3 weight percent of said secondary-alkyl substituted benzene hydroperoxide.

8. A process according to claim 1 wherein said secondary-alkyl substituted benzene hydroperoxide is cyclohexylbenzene hydroperoxide and said solvent is acetone.

9. A process according to claim 1 wherein said secondary-alkyl substituted benzene hydroperoxide is cyclohexylbenzene and said solvent is methylethyl ketone.

* * * * *